United States Patent [19]

Wetzel et al.

[11] 4,362,725

[45] Dec. 7, 1982

[54] CEPHALOSPORINS

[75] Inventors: Bernd Wetzel; Eberhard Woitun, both of Biberach an der Riss; Wolfgang Reuter, Laupertshausen; Roland Maier, Biberach an der Riss; Uwe Lechner, Ummendorf; Hanns Goeth, Biberach an der Riss, all of Fed. Rep. of Germany

[73] Assignee: Dr. Karl Thomae Gesellschaft mit beschränkter Haftung, Biberach, Fed. Rep. of Germany

[21] Appl. No.: 305,953

[22] Filed: Sep. 28, 1981

[30] Foreign Application Priority Data

Oct. 11, 1980 [DE] Fed. Rep. of Germany ....... 3038501

[51] Int. Cl.³ .................. A61K 31/545; C07D 501/56
[52] U.S. Cl. ..................................... 424/246; 544/21; 544/23; 544/27
[58] Field of Search ............................ 544/27, 21, 23; 424/246

[56] References Cited

U.S. PATENT DOCUMENTS 4,316,898 2/1982 Wetzel et al. ..................... 544/27

Primary Examiner—Paul M. Coughlan, Jr.
Attorney, Agent, or Firm—Hammond & Littell, Weissenberger & Muserlian

[57] ABSTRACT

Compounds of the formula

A—CH—CONH—[β-lactam-cephem structure with Y, S, N, CH₂SHet, COOE substituents]
  |
  NH
  |
  CO
  |
  NH—[dihydropyrimidine ring with OH, N, N, R]

wherein

A is phenyl, 4-hydroxy-phenyl, 2-thienyl, 2-furyl or 3,4-dihydroxy-phenyl;
Y is hydrogen or methoxy;
Het is 4H-5,6-dioxo-1,2,4-triazin-3-yl, 4-methyl-5,6-dioxo-1,2,4-triazin-3-yl, 2-methyl-5,6-dioxo-1,2,4-triazin-3-yl, 1-vinyl-tetrazol-5-yl, 1-allyl-tetrazol-5-yl or

[tetrazole ring structure with $(CH_2)_nR_1$ substituent]

where
n is an integer from 1 to 3, inclusive
$R_1$ is hydroxyl, amino, dimethylamino, acetylamino, aminocarbonyl, aminocarbonylamino, aminosulfonyl, aminosulfonylamino, methylcarbonyl, methylsulfonylamino, cyano, hydroxysulfonylamino, methylsulfonyl, methylsulfinyl, a carboxylic acid group or a sulfonic acid group, and
—$(CH_2)_n$—$R_1$ may also be alkyl of 2 to 4 carbon atoms or 2,3-dihydroxy-propyl;
R is cyclopropyl, 4'-hydroxycyclohexyl-amino $$N\diagup\!\!\!\!\diagdown\begin{smallmatrix}R_2\\H\end{smallmatrix}, -NH-CH_2-CH_2-G, -NH-(CH_2)_3-G \text{ or}$$

$$-NH-(CH_2)_m-\text{[phenyl with }R_3, R_4\text{]}$$

where
$R_2$ is straight or branched, saturated or unsaturated hydrocarbyl of 1 to 4 carbon atoms or cycloalkyl of 3 to 6 carbon atoms;
G is hydroxyl, aminocarbonyl, aminosulfonyl, aminocarbonylamino, acetylamino, methylsulfonylamino, methylsulfinyl or methylsulfonyl;
m is 0 or 1; and
$R_3$ and $R_4$, which may be identical to or different from each other, are each hydrogen, chlorine, fluorine, hydroxyl, methoxy, acetylamino, aminocarbonylamino, nitro, acetyl, methylcarbonyloxy, methoxycarbonyl, aminocarbonyl, cyano, methylsulfinyl, methylsulfonyl, aminosulfonyl, methylaminosulfonyl or methyl; and
E is hydrogen or a protective group which is easily removable in vitro or in vivo;

and, when E is hydrogen, non-toxic, pharmacologically acceptable salts thereof; the compounds as well as their salts are useful as antibiotics.

14 Claims, No Drawings

CEPHALOSPORINS

This invention relates to novel cephalosporins and salts thereof, to methods of preparing these compounds, to pharmaceutical compositions containing them as active ingredients, and to methods of using them as antibiotics.

More particularly, the present invention relates to a novel class of cephalosporins represented by the formula $$
\begin{array}{c}
\overset{*}{A}-CH-CONH \\
\mid \\
NH \\
\mid \\
CO \\
\mid \\
NH
\end{array}
\quad (I)
$$

(structure with Y, S ring, CH$_2$SHet, COOE, OH, N=N ring with R)

wherein

A is phenyl, 4-hydroxy-phenyl, 2-thienyl, 2-furyl or 3,4-dihydroxy-phenyl;

Y is hydrogen or methoxy;

Het is 4H-5,6-dioxo-1,2,4-triazin-3-yl, 4-methyl-5,6-dioxo-1,2,4-triazin-3-yl, 2-methyl-5,6-dioxo-1,2,4-triazin-3-yl, 1-vinyl-tetrazol-5-yl, 1-allyl-tetrazol-5-yl or $$
\begin{array}{c}
N \longrightarrow N \\
\parallel \\
\diagdown \diagup N \\
N \\
\mid \\
(CH_2)_n R_1
\end{array}
$$

where n is an integer from 1 to 3, inclusive $R_1$ is hydroxyl, amino, dimethylamino, acetylamino, aminocarbonyl, aminocarbonylamino, aminosulfonyl, aminosulfonylamino, methylcarbonyl, methylsulfonylamino, cyano, hydroxysulfonylamino, methylsulfonyl, methylsulfinyl, a carboxylic acid group or a sulfonic acid group, and —(CH$_2$)$_n$—R$_1$ may also be alkyl of 2 to 4 carbon atoms or 2,3-dihydroxy-propyl;

R is cyclopropyl, 4'-hydroxycyclohexyl-amino, $$
-N\begin{matrix} R_2 \\ \diagdown \\ H \end{matrix}, \; -NH-CH_2-CH_2-G, \; -NH-(CH_2)_3-G \text{ or}
$$

$$
-NH-(CH_2)_m-\underset{R_4}{\overset{R_3}{\diagup\phantom{xx}\diagdown}}
$$

where $R_2$ is straight or branched, saturated or unsaturated hydrocarbyl of 1 to 4 carbon atoms or cycloalkyl of 3 to 6 carbon atoms;

G is hydroxyl, aminocarbonyl, aminosulfonyl, aminocarbonylamino, acetylamino, methylsulfonylamino, methylsulfinyl or methylsulfonyl;

m is 0 or 1; and $R_3$ and $R_4$, which may be identical to or different from each other, are each hydrogen, chlorine, fluorine, hydroxyl, methoxy, acetylamino, aminocarbonylamino, nitro, acetyl, methylcarbonyloxy, methoxycarbonyl, aminocarbonyl, cyano, methylsulfinyl, methylsulfonyl, aminosulfonyl, methylaminosulfonyl or methyl; and E is hydrogen or a protective group which is easily removable in vitro or in vivo, such as those which have heretofore been used in the field of penicillins and cephalosporins, especially ester-forming groups which can be removed under mild conditions by hydrogenation of hydrolysis or other treatments, or ester-forming groups which can easily be split off in the living organism;

and, when E is hydrogen, non-toxic, pharmacologically acceptable salts thereof, such as their alkali metal or alkaline earth metal salts, especially the sodium, potassium, magnesium or calcium salts; their ammonium salts; or their organic amine salts, especially the triethylamine or dicyclohexylamine salts.

In vitro easily removable protective groups are, for example, benzyl, diphenylmethyl, trityl, tert. butyl, 2,2,2-trichloroethyl or trimethylsilyl.

In vivo easily removable protective groups are, for example, alkanoyloxyalkyl, such as acetoxymethyl, propionyloxymethyl, 2-acetoxyethyl or pivaloyloxymethyl, phthalidyl or indanyl.

A preferred sub-genus is constituted by those compounds of the formula I wherein A, Y and Het have the meanings previously defined;

R is p-aminosulfonyl-m-hydroxy-anilino, cyclopropyl, propylamino, isopropylamino, cyclopentylamino, cyclohexylamino, 3'-hydroxypropyl-amino, 4'-hydroxycyclohexyl-amino, 2'-aminosulfonylethylamino or $$
-NH-(CH_2)_m-\underset{\phantom{xx}}{\overset{R^3}{\diagup\phantom{xx}\diagdown}}
$$

where m is 0 or 1; and $R_3$ is hydrogen, hydroxyl, nitro, acetylamino, methylsulfinyl, methylsulfonyl, acetyl, aminocarbonyl, aminocarbonylamino, aminosulfonyl or methylaminosulfonyl; and E is hydrogen;

and non-toxic, pharmacologically acceptable salts thereof.

The cephalosporin compounds of the formua I exist in two tautomeric forms, that is, the lactim and the lactam form. Which of the two forms I or I' is predominant, depends particularly on the respective solvent and on the type of substituent R:

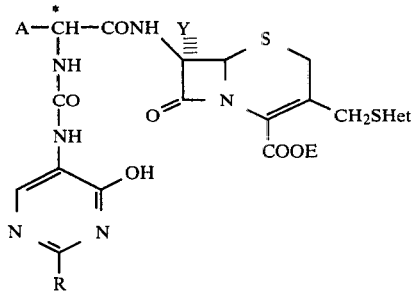

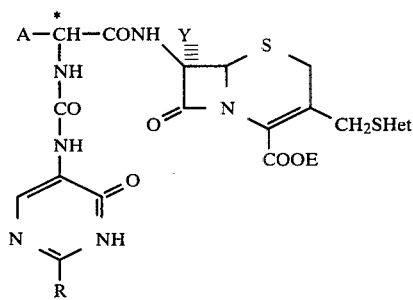

It goes without saying that the compounds of the formula I referred to above always comprise both tautomeric forms.

With regard to the chiral centre $\overset{*}{\text{C}}$, the compounds of the formula I may be present in two possible R- and S-configurations or as mixtures of these. Particularly preferred are those compounds which have the D=R configuration. If the end product is obtained in the D,L-form, the pure D- and L-diastereoisomers can be separated by preparative high pressure liquid chromatography (HPLC).

The compounds of the formula I may be prepared by the following methods.

Method A:
By reacting a compound of the formula

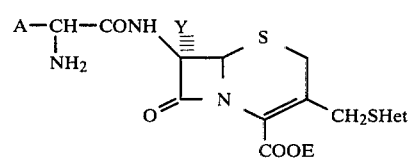

wherein
A, Y, Het and E have the meanings previously defined, with a pyrimidine derivative of the formula

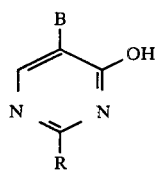

wherein
R has the meanings previously defined, and

B is =NCO or a derivative of —NHCOOH, such as —NHCOCl, —NHCOBr or

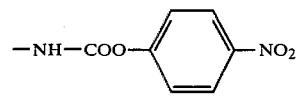

where =NCO and —NHCOCl are especially preferred.

Also mixtures of such pyrimidine derivatives of the formula III can be used, wherein B has partly the one and partly the other of the above-mentioned meanings, for instance =NCO and —NHCOCl simultaneously.

When E is hydrogen, the starting compounds of the formula II can be used in form of their inorganic or organic salts, for instance as the triethylammonium salts or the sodium salts. In that case the reaction can be carried out in any desired mixtures of water and those organic solvent which are miscible with water such as ketones, for example acetone; cyclic ethers, for example tetrahydrofuran or dioxane; nitriles, for example acetonitril; formamides, for example dimethylformamide; dimethylsulfoxide; or alcohols, for example isopropanol; or in hexametalpol. By addition of a base or by use of a buffer solution, the pH of the reaction mixture is kept in a pH range of about 2.0 to 9.0, preferably between pH 6.5 and 8.0. However, it is also possible to carry out the reaction in an anhydrous organic solvent, such as halogenated hydrocarbons like chloroform or methylene chloride, in the presence of a base, preferably triethylamine, diethylamine or N-ethylpiperidine.

The reaction can further be carried out in a mixture of water and a water-immiscible solvent, such as an ether, for example diethyl ether; a halogenated hydrocarbon, for example chloroform or methylene chloride; carbon disulfide; a ketone, for example isobutylmethyl ketone; an ester, for example ethyl acetate; or an aromatic solvent, for example benzene, where it is advantageous to stir vigorously and to keep the pH value in a range of about pH 2.0 to 9.0, preferably between 6.5 and 8.0, by addition of a base or by use of a buffer solution. The reaction can be carried out, however, also in water alone in the presence of an organic or inorganic base or of a buffer substance.

When E is trimethylsilyl, that is, if a silyl derivative of a compound of the formula II, such as a mono- or, more advantageously, a di-trimethylsilyl derivative silylated at the amino and carboxyl group, is used as the starting compound, and it is reacted with a compound of the formula III, the reaction is generally advantageously carried out in an anhydrous solvent or a solvent free from hydroxyl groups, for example in a halogenated hydrocarbon, such as methylene chloride or chloroform, benzene, tetrahydrofuran, acetone or dimethylformamide, etc. The addition of a base is not essential, but may be of advantage in individual cases to improve the yield or the purity of the end product. Examples of such bases are tertiary aliphatic or aromatic amines, such as pyridine or triethylamine, or by steric hindrance difficultly acylatable secondary amines, such as dicyclohexylamine.

When E is one of the above-mentioned in vitro or in vivo easily removable protective groups, such as diphenylmethyl or pivaloyloxymethyl, it is of advantage to perform the reaction in an aprotic solvent, such as absolute methylene chloride, chloroform, tetrahydrofuran or dimethylformamide.

The amount of base to be used is determined, for example, by the desired maintenance of a certain pH value.

Where no pH measurement or adjustment is made or where no measurement is possible or practical because of a lack of sufficient water in the diluting agent, 1.0 to 2.0 mol-equivalents of base are used when silylated compounds of the formula II are not present. When such silylated compounds are present, preferably up to one mol-equivalent of base is used.

In general, all organic and inorganic bases which are usually used in organic chemistry, can be used as base additives. Such bases may be alkali metal and alkaline earth metal hydroxides, alkaline earth metal oxides, alkali metal and alkaline earth metal carbonates and bicarbonates, ammonia, primary, secondary and tertiary aliphatic and aromatic amines, as well as heterocyclic bases. Preferred bases are sodium, potassium and calcium hydroxide, calcium oxide, sodium and potassium carbonate, sodium and potassium bicarbonate, ethylamine, methylethylamine, triethylamine, hydroxyethylamine, aniline, dimethylaniline, pyridine and piperidine. When using silylated starting compounds, however, the above-mentioned restrictions concerning the kind of base should be considered.

Suitable buffer systems include all the usual buffer mixtures, such as phosphate buffer, citrate buffer and tris(hydroxymethyl)-amino-methane buffer.

The reaction temperatures can be varied over a wide range. In general, the reaction is carried out between $-20°$ and $+50°$ C., preferably between $0°$ and $+20°$ C.

The reaction partners of the formulas II and III can be reacted with each other in equimolar quantities. However, in some cases it may be advantageous to use one of the reaction partners in excess to facilitate the purification of the end product or to increase the yield.

Method B:

By reacting a ureidocarboxylic acid of the formula

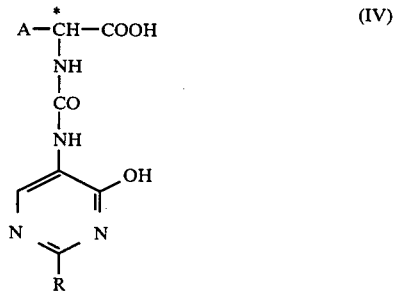

(IV)

wherein

A and B have the meanings previously defined, or a salt of reactive derivative thereof, with a 7-aminocephalosporanic acid derivative of the formula

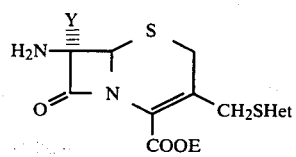

(V)

wherein

E, Y and Het have the meanings previously defined.

Suitable reactive derivatives of the ureidocarboxylic acids of the formula IV include, for example, their acid anhydrides such as those derived from chloroformates, for instance ethyl or isobutyl chloroformate, or their reactive esters such as the p-nitrophenyl ester or the N-hydroxysuccinimide ester, or their reactive amides such as the N-carbonyl-imidazole, but also their acid halides such as the corresponding acid chloride or their acid azides.

In general, however, all methods of bonding which are known in β-lactam chemistry can be used.

The 7-aminocephalosporanic acid derivative is advantageously reacted in the form of an in vitro or in vivo easily cleavable derivative. For example, the compounds of the formula V wherein E has the above-mentioned meanings, with the exception of hydrogen, are suitable; especially preferred derivatives are the diphenylmethyl ester, the tert. butyl ester, the trimethylsilyl ester or the N,O-bistrimethylsilyl derivative.

For example, the ureidocarboxylic acid or a salt or reactive derivative thereof is reacted with the 7-aminocephalosporanic acid derivative in a solvent at temperatures between $-40°$ and $+40°$ C., optionally in the presence of a base. If, for example, an anhydride of the ureidocarboxylic acid, such as the anhydride with ethylchloroformate, is used, the reaction is carried out while cooling, for instance at $-10°$ C. to $+10°$ C., in the presence of a tertiary amine such as triethylamine or N,N-dimethylaniline, in a solvent such as acetone, tetrahydrofuran, dimethylformamide, chloroform, dichloromethane, hexametapol, or a mixture of these solvents. If, for example, an N-hydroxysuccinimide ester of the ureidocarboxylic acid is reacted with a derivative of the formula V, the reaction is preferably carried out at $0°$ to $20°$ C. in the presence of a base such as triethylamine, in a solvent such as dimethylformamide, dichloromethane, dioxane, or a mixture of such solvents.

The reaction of ureidocarboxylic acid of the formula IV or a salt thereof with a compound of the formula V is advantageously carried out in the presence of a condensation agent, for instance in the presence of N,N'-dicyclohexylcarbodiimide.

Method C:

By reacting a compound of the formula

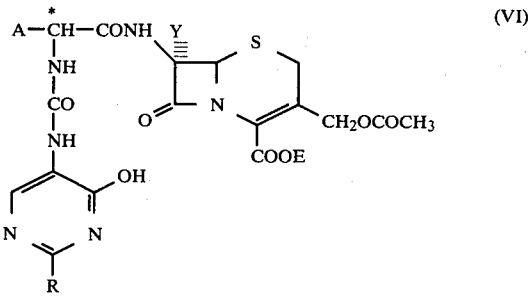

(VI)

wherein

A, R and Y have the meanings previously defined, and E is hydrogen with a compound of the formula

Het—S—M (VII)

wherein

Het has the meanings previously defined, and

M is hydrogen, an alkali metal or an alkaline earth metal.

For example, a compound of the formula VI is reacted with 5-vinyl-2-mercapto-1,2,3,4-tetrazole in a solvent such as water, methanol, ethanol, acetone, methyl ethyl ketone, tetrahydrofuran, acetonitrile, ethyl acetate, dimethoxyethane, dimethylformamide, dimethyl sulfoxide, chloroform or a mixture of these solvents. Preferably, a strong polar solvent such as water or the like is used. In this case the pH of the reaction solution is advantageously maintained between 2 and 10, and particularly between 4 and 8. The desired pH value can be adjusted by addition of a buffer solution, such as sodium phosphate. The reaction conditions are not subject to special restrictions. Normally, the reaction is carried out at a temperature in a range of 0° to 100° C., over a reaction time of several hours.

Method D:

A compound of the formula I wherein Y is methoxy can be obtained by reacting a compound of the formula I wherein Y is hydrogen, in the presence of methanol with an alkali metal methylate of the formula $M^+OCH_3^-$, where $M^+$ is an alkali metal, and then with a halogenating agent. For this purpose, a cephalosporin of the formula I wherein Y is hydrogen is dissolved or suspended in an insert solvent, such as tetrahydrofuran, dioxane, ethyleneglycol dimethylether, methylene chloride, chloroform, dimethyl formamide, methanol or the like or in a mixture of two of these solvents.

An alkali metal methylate together with methanol is added to the obtained solution or suspension. The obtained mixture is caused to react, and the reaction mixture is then reacted with a halogenating agent. In this reaction methanol is used in excess, and the quantity of the alkali metal methylate is preferably 2 to 6 equivalents per equivalent of cephalosporin. "Excess" means an amount of more tha one equivalent per equivalent of cephalosporin. All reactions are carried out at temperatures between −120° and −10° C., and preferably between −100° and −50° C. A reaction time of 5 to 30 minutes is sufficient. The reaction is terminated by acidifying the reaction system.

The halogenating agent used in this process is generally known as a source for positive halogen atoms, such as $Cl^+$, $Br^+$ or $I^+$. Examples of such halogenating agents are halogens, such as chlorine, bromine, etc.; N-halo-imides, such as N-chloro-succinimide, N-bromo-succinimide, and the like; N-halo-amides, such as N-chloroacetamide, N-bromo-acetamide, etc.; N-halo-sulfonamides, such as N-chloro-benzene-sulfonamide, N-chloro-p-toluenesulfonamide, etc.; 1-halo-benzotriazoles; 1-halo-triazines; organic hypohalites, such as tert. butylhypochlorite, tert. butylhypoiodite, etc.; and halo-hydantoins, such as N,N-dibromohydantoin, etc. Tert. butylhypochlorite is preferred among these halogenating agents. The halogenating agent is used in a quantity sufficient to release an equivalent quantity of positive halogen atoms with regard to the amount of cephalosporin of the formula VI.

Suitable acids for termination of the reaction are those which do not lead to solidification of the reaction mixture or to freezing of the reaction mixture into a heavy viscous mass when they are added to the cold reaction mixture. Suitable acids are, for example, 98% formic acid, glacial acetic acid, trichloroacetic acid or methane sulfonic acid.

After termination of the reaction the excess halogenating agent is removed by treatment with a reducing agent, such as trialkyl phosphite, sodium thiosulfate or the like.

The compounds prepared according to methods A, B and D, wherein E is an in vitro easily removable protective group, can be converted according to known methods in cephalosporin chemistry into the free carboxylic acids of the formula I wherein E is hydrogen. Thus, the trimethylsilyl group can, for example, be easily removed by aqueous hydrolysis, and the benzhydryl group can be removed, for example, by hydrolytic cleavage with trifluoroacetic acid. This elimination of the protective groups is known from the literature.

Moreover, the cephalosporin antibiotics of the formula I wherein E is hydrogen can be converted into the acyloxyalkyl esters, wherein E is, for example a pivaloyloxymethyl radical

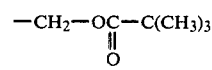

by reacting an alkali metal salt of the cephalosporin carboxylic acid, for example a sodium or potassium salt, with a pivaloyloxymethyl halide of the formula

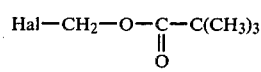

wherein Hal is chlorine, bromine or iodine.

Further suitable acyloxyalkyl halides are, for example, chloromethyl acetate, bromomethylpropionate or 1-bromoethyl acetate.

The preparation of an acyloxyalkyl ester of the formula I is carried out by reacting the respective alkali metal salt of the parent acid in an inert solvent with a slight molar excess of the iodine, bromine or chloroalkyl ester, such as pivaloyloxymethyl iodide, at room temperature or slightly elevated temperature up to about 40° to 45° C. Suitable solvent are, for example, acetone, tetrahydrofuran, dioxane, dimethylformamide or methylene chloride.

An indanyl ester of the formula I, wherein E is

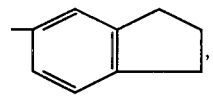

can be prepared by reacting 5-indanol in an inert solvent, such as dioxane or tetrahydrofuran, with the free acid form of a compound of the formula I, wherein E is hydrogen, in the presence of a condensation agent, for example a diimide such as dicyclohexyl-carbodiimide. The reaction is carried out while stirring at a temperature of about 20° to 35° C. during a reaction time of about 6 to 8 hours. For the isolation of the indanyl ester, the reaction mixture is first diluted with water, and the insoluble dicyclohexylurea is filtered off from the reaction mixture. Then, the ester is extracted from the filtrate.

The indanyl esters can also be prepared by reacting an anhydride, formed from a cephalosporanic acid of the formula I and acetic acid, with 5-indanol.

A phthalidyl ester of the formula I, wherein $R_3$ is

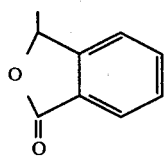

can be prepared by reacting the bromophthalide of the formula

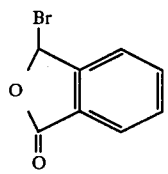

with a salt of a cephalosporanic acid of the formula I. The esterification can be effected by slowly heating a mixture of equimolar amounts of the cephalosporin salt, such as the sodium or potassium salt, and bromophthalide in dimethylformamide, dimethylacetamide, dioxane, tetrahydrofuran or mixtures thereof.

After the reaction has gone to completion, the reaction mixtures obtained according to methods A-D are further processed by conventional methods for β-lactam antibiotics. The same is the case concerning the isolation and purification of the end products, for instance concerning the liberation of the acid to form other salts with inorganic or organic bases. Especially suitable for the preparation of potassium or sodium salts is the precipitation of these salts from an alcoholic-ethereal solution of a free acid by addition of potassium or sodium 2-ethylhexanoate, or the reaction of a free acid with the corresponding quantity of sodium bicarbonate under pH control and subsequent freeze-drying.

Typical starting compounds of the formulas II and V, wherein A is phenyl, substituted phenyl or thienyl, and Het is 1-methyl-1H-tetrazol-5-yl are known from the literature; see, for example, published European Application No. 100, and German Offenlegungsschriften Nos. 2,934,682 and 2,936,434. For example, 7-aminocephalosporanic acid systems of the type in question can be obtained by reacting 7-aminocephalosporanic acid with the corresponding mercaptoheterocycle in conventional manner.

The starting compounds of the formula III can be obtained, for example, by reacting a corresponding 5-aminopyrimidine of the formula

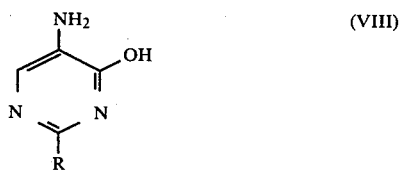

wherein R has the meanings previously defined, with phosgene. This reaction is preferably carried out in a solvent which does not contain hydroxyl groups, such as tetrahydrofuran, methylene chloride, chloroform, dimethoxyethane or hexametapol, at temperatures between −40° and +60° C., preferably between −10° and +20° C. It is recommended to neutralize the hydrogen chloride released by the reaction with equimolar quantities of an inert organic base, such as triethylamine or pyridine. Also, pyridine in excess can be used as the solvent. If the particular aminopyrimidine of the formula VIII is difficultly soluble in one of the mentioned solvents, the phosgenation can also be carried out in a heterogeneous system. In an especially preferred manner, the aminopyrimidine of the formula VIII can be converted by treatment with a silylating agent, such as hexamethyldisilazane, trimethyl chlorosilane/triethylamine, trimethylsilyl diethylamine or N,O-bis-trimethylsilyl acetamide, into an aminopyrimidine which, in general, is very easily soluble in the mentioned solvents and which is, depending on the number of exchangeable hydrogen atoms, mono- or poly-silylated. After addition of phosgene, the aminopyrimidine reacts with the corresponding compound of the formula III, where the reaction is preferably carried out without the addition of a base.

Depending on the kind of solvent, the temperature, the amount and kind of base which is optionally added, either mainly the corresponding isocyanate or the carbamic acid halide or a mixture of these two compounds is obtained. Depending on the conditions, the isocyanate of the formula III can also be present as a dihydrooxazolo-pyridimine of the formula IIIa, this compound being isomeric with the isocyanate.

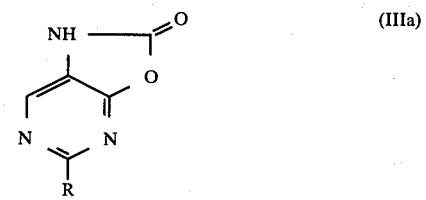

Depending on the kind of the substituent R, the isocyanate of the formula VI may also be present as a mono- or poly-silylated analog.

The starting compounds of the formula III or IIIa or mixtures thereof or silylated analogs thereof obtained by phosgenation, as described above, are in general readily soluble in the above-mentioned solvents, and after removal of excess phosgene they can be treated directly without further purification with the corresponding cephalosporin derivative of the formula II.

However, it is also possible to isolate the intermediate product of the formula IIIa, de-silylate the intermediate, optionally with a protic solvent such as water or methanol, or, based on the properties of solubility, to purify it or react it in the manner mentioned above.

The syntheses for 2-substituted 5-amino-4-hydroxypyrimidines of the formula VIII are described in the German Offenlegungsschriften Nos. 2,808,153 and 2,910,190.

The ureidocarboxylic acids of the formula IV can be easily obtained by reacting a pyrimidine derivative of the formula III with a glycine derivative of the formula

wherein A has the meanings previously defined. The reaction is carried out at temperatures between −20° and +40° C., preferably between 0° and +20° C., in a solvent. Suitable solvents are, for example, mixtures of water and organic solvents which are miscible with water, such as acetone, tetrahydrofuran, dioxane, acetonitrile, dimethylformamide, ethanol or dimethylsulfoxide, optionally in the presence of a hydrogen-halide-binding agent. Suitable representatives thereof are, for example, trialkylamines such as triethylamine, or inorganic bases such as dilute sodium hydroxide.

The ureidocarboxylic acids of the formula IV are disclosed in German Offenlegungsschrift No. 2,924,948, as is the synthesis of the starting compounds of the formula VI.

The following examples illustrate the present invention and will enable others skilled in the art to understand it more completely. It should be understood, however, that the invention is not limited solely to the particular examples given below.

EXAMPLE 1

Sodium 7-{D-α-[3-(2-p-aminosulfonylanilino-4-hydroxy-5-pyrimidinyl)-ureido]-p-hydroxyphenylacetamido}-3-[(1-vinyltetrazol-5-yl)-thiomethyl]-ceph-3-em-4-carboxylate 2.37 gm (0.005 mol) of D-α[3-(2-p-aminosulfonylanilino-4-hydroxy-5-pyrimidinyl)-ureido]-p-hydroxyphenylacetic acid were dissolved in 30 ml of dry dimethylformamide. A solution of 2.53 gm (0.005 mol) of diphenylmethyl 7-amino-3-[(1-vinyl-tetrazol-5-yl)-thiomethyl]-ceph-3-em-4-carboxylate in 30 ml of dry methylene chloride was then added to the resulting solution. 1.13 gm of dicyclohexyl-carbodiimide were added to the solution thus formed while cooling with ice, followed by stirring of the mixture for 2 hours at 10° C. and then for 6 hours at room temperature. A thin-layer chromatogram showed that the starting products had almost completely disappeared. After filtration, the filtrate was concentrated in vacuo to dryness and then extracted by thorough stirring twice with 50 ml of methanol and once with 100 ml of methylene chloride. The solid product left behind was suction-filtered off and washed thoroughly with ether. To remove minor impurities, which remain on the starting spot in the thin-layer chromatogram (methylene chloride:methanol 5:1), the product was chromatographed on a silicagel column. Yield of ester: 3.46 g (72%).

The product thus obtained was suspended in a little methylene chloride, and the resulting suspension was stirred for 30 minutes, while cooling with ice, with 2 ml of anisole and 10 ml of trifluoroacetic acid, whereby a solution was formed. 50 ml of toluene were then added twice, the solution being evaporated in vacuo to dryness after each addition. Following the addition of ether, the product was suction-filtered off.

To prepare the sodium salt, the product was dissolved in a little dimethylformamide, the calculated quantity of sodium ethylhexanoate in methanol was added and the mixture was admixed with ether. The precipitated product was suction-filtered off, washed carefully with ether and dried in vacuo. Yield of sodium salt (based on the cephalosporin derivative used): 2.71 gm (66%). IR-spectrum: 1760, 1655, 1615, 1550 cm$^{-1}$; NMR-sectrum (DMSO+CD$_3$OD) signals at ppm: 3.45 (m,2H), 4.35 (m,2H), 4.85 (d,1H), 5.40–5.90 (m, 4H), 6.6–7.0 (m, 2+1H), 7.15 (d, 2H), 7.7 (d, 2H), 8.0 (d,2H), 8.37 (s,1H).

The cephalosporins listed in the following table were also synthesized by the method described in Example 1.

| Example | A | R | Y | Het | Yield % | IR-spectrum (cm$^{-1}$) | NMR-spectrum (DMSO + CD$_3$OD). signals at ppm: |
|---|---|---|---|---|---|---|---|
| 2 | HO—⌬— | —NH—⌬—SO$_2$NH$_2$ | H | N—N, N—N ring with CH$_2$CH$_2$N(CH$_3$)$_2$ | 48.5 | 1760 1650 1610 | 2.25 (s,6H), 2.75 (t,2H), 3.60 (m,2H), 4.30 (m,4H), 4.85 (d,1H), 5.40 (s,1H), 5.55 (d,1H), 6.75 d,2H), 7.25 (d,2H), 7.75 (d,2H), 8.0 (d,2H), 8.38 (s,1H). |
| 3 | HO—⌬— | —NH—⌬—SO$_2$NH$_2$ | H | N—N, N—N ring with CH$_2$CH$_2$OH | 44 | 1760 1660 1610 | 3.6 (m,2H), 3.80 (m,2H), 4.35 (m,4H), 4.95 (d,1H), 5.40 (s,1H), 5.70 (d,1H), 6.75 (d,2H), 7.25 (d,2H), 7.70 (d,2H), 8.0 (d,2H), 8.36 (s,1H). |
| 4 | ⌬$_S$— | —NH—⌬—SO$_2$NH$_2$ | H | N—N, N—N ring with CH=CH$_2$ | 52 | 1760 1650 1600 | 3.45(m,2H), 4.35 (m,2H), 4.95 (dd,1H), 5.50–5.90 (m,4H) 6.7–7.2 (m,3H), 7.35 (m,1H), 7.7 (d,2H), 8.0 (d,2H), 8.35 (s,1H). |
| 5 | HO—⌬— | —NH—⌬—OH | H | N—N, N—N ring with CH$_2$=CH$_2$ | 58 | 1760 1650 1600 | 1.75 (m,8H), 3.4–3.8 (m,1+1H+2H), 4.4 (m,2H), 4.85 (d,1H), 5.40–5.90 (m,4H), 6.60–7.0 (m,3H), 7.25 (d,2H) 7.70 (d,2H), 8.0 (d,2H), 8.35 (s,1H) |

EXAMPLE 6

Sodium 7-{D-α-[3-(2-p-aminosulfonylanilino-4-hydroxy-5-pyrimidinyl)-ureido]-p-hydroxyphenylacetamido}-3-[(1-allyltetrazol-5-yl)-thiomethyl]-ceph-3-em-4-carboxylate 0.2 gm of N-methyl-morpholine was added to a solution of 950 mgm (0.002 mol) of the ureidocarboxylic acid used in Example 1 in 20 ml of dry dimethylformamide. The solution was cooled to $-15°$ C., and a solution of 0.22 gm of ethyl chloroformate in 5 ml of methylene chloride was added dropwise at that temperature. The mixture thus obtained was kept at the temperature of $-15°$ C. for 45 minutes. A solution of 1.04 gm (002 mol) of diphenylmethyl 7-amino-3-[(1-allyltetrazol-5-yl)-thiomethyl]-ceph-3-em-4-carboxylate in 20 ml of anhydrous methylene chloride was then added dropwise at $-15°$. After stirring for one hour at $-10°$ C., the mixture was allowed to return slowly to room temperature. The solution was then evaporated in vacuo to dryness and then further treated in the same way as described in Example 1. The protective ester group was also removed in the same way as in Example 1. Yield of sodium salt: 900 mgm (54%).

IR-spectrum: 1760, 1650, 1610, 1550 cm$^{-1}$; NMR-spectrum (DMSO+CD$_3$OD) signals at ppm: 3.60 (m,2H), 4.25 (m, 2H), 4.80-5.60 (m, 6H), 5.70-6.40 (m, 2H), 6.75 (d, 2H), 7.25 (d,2H), 7.70 (d,2H), 8.0 (d, 2H), 8.36 (s, 1H).

The following cephalosporins were also synthesized by the method described in Example 6:

EXAMPLE 10

7-{D-α-[3-(2-p-aminosulfonylanilino-4-hydroxy-5-pyrimidinyl)ureido]-p-hydroxyphenylacetamido}-3-[(1-hydroxysulfonylmethyl-tetrazol-5-yl)-thiomethyl]-ceph-3-em-4-carboxylic acid The activated anhydride was produced in the same way as in Example 6 from 475 mgm (0.001 mol) of the ureido carboxylic acid used in Example 1 using N-methyl-morpholine and ethyl chloroformate. At the same time, 600 mgm of N,O-bis-trimethylsilyl-acetamide were added to a suspension of 410 gm (0.001 mol) of 7-amino-3-[(1-hydroxysulfonylmethyltetrazol-5-yl)-thiomethyl]-ceph-3-em-4-carboxylic acid in 20 ml of anhydrous acetonitrile, whereby a solution was obtained. This solution was cooled to $-15°$ C. and added dropwise to the above-mentioned activated anhydride solution at that temperature. The mixture was then stirred for 1 hour at $-10°$ C. and for 1 hour at $+10°$ C. Thereafter, 2 ml of methanol were added, and the insoluble material was removed by filtration. The solvent was then removed in vacuo. The residue was taken up in 40 ml of water, and the solution was adjusted to pH 7.0. At that pH-value the solution was extracted twice with ethyl acetate. The aqueous phase was adjusted to pH 2.9 by the addition of dilute hydrochloric acid while cooling with ice, and the precipitated product was suction-filtered off, washed with a little water and dried in vacuo. Yield: 435 mgm (59%).

IR-spectrum: 1760, 1660, 1600 cm$^{-1}$; NMR-spectrum (DMSO+CD$_3$OD) signals at ppm: 3.60 (m, 2H), 4.25 (m, 2H), 5.0 (m, 3H), 5.55 (s, 1H), 5.70 (d, 1H), 6.75 (d, 2H), 7.25 (d, 2H), 7.85 (m, 4H), 8.37 (s, 1H).

The following cephalosporins were also synthesized by by the method described in Example 10.

| Example | A | R | Y | Het | Yield % | IR-spectrum (cm$^{-1}$) | NMR-spectrum (DMSO + CD$_3$OD). at ppm: |
|---|---|---|---|---|---|---|---|
| 7 | HO—⟨phenyl⟩— | —NH—⟨phenyl⟩—SO$_2$NH$_2$ | H | tetrazole with N-CH$_2$COOH | 45 | 1760, 1650, 1610 | 3.6 (m,2H), 4.3 (m,2H), 5.0 (m,2+1H), 5.55 (s,1H), 5.70 (d,1H), 6.75 (d,2H), 7.30 (d,2H), 7.85 (m,4H) 8.24 (s,1H). |
| 8 | HO—⟨phenyl⟩— | —NH—⟨phenyl⟩—OH | H | tetrazole with N-CH$_2$NHSO$_3$H | 52 | 1760, 1660, 1605 | 3.55 (m,2H), 4.35 (m,2H), 4.8 (s,2H), 4.95 (d,1H), 5.50 (s,1H),5,65 (d,1H), 6.75 (d,2H), 7.15 (d,2H), 7.45 (d,2H), 7.85 (d,2H), 8.30 (s,1H). |
| 9 | HO—⟨phenyl⟩— | —NHCH$_2$—⟨phenyl⟩—OH | H | tetrazole with N-CH$_2$CH$_2$NHCONH$_2$ | 58 | 1760, 1660, 1600 | 3.0 (m,2H), 3.50 (m,2H), 4.4 (m,6H), 4.90 (d,1H), 5.55 (d,1H), 5.70 (d,1H), 6.85 (d,2H), 7.15-7.6 (m,6H), 8.05 (s,1H). |

| Example | A | R | Y | Het | Yield % | IR-spectrum (cm$^{-1}$) | NMR-spectrum (DMSO + CD$_3$OD) Signals at ppm: |
|---|---|---|---|---|---|---|---|
| 11 | HO—⟨⟩— | —NH—⟨⟩—SO$_2$NH$_2$ | H | triazole with CH$_2$CONH$_2$ | 58.5 | 1760 1660 1615 | 3.60 (m,2H), 4.35 (m,2H), 5.0 (m,2+1H), 5.50 (s,1H), 5.65 (d,1H), 6.75 (d,2H), 7.25 (d,2H), 7.7 (d,2H), 8.0 (d,2H), 8.30 (s,1H). |
| 12 | HO—⟨⟩— | —NH—⟨⟩—SO$_2$NH$_2$ | H | triazole with CH$_2$CH$_2$NHSO$_2$NH$_2$ | 49 | 1760 1650 1610 | 2.95(m,2H), 3.50 (m,2H), 4.4 (m,4H), 4.95 (d,1H), 5.55 (s,1H), 5.70 (d,1H), 6.85 (d,2H), 7.25 (d,2H), 7.70 (d,2H), 8.0 (d,2H), 8.35 (s,1H). |
| 13 | HO—⟨⟩— | —NH—CH$_2$CH$_2$SO$_2$NH$_2$ | H | triazole with CH$_2$CH$_2$NHCOCH$_3$ | 41 | 1760 1660 1600 | 1.85(s,3H), 3.0 (m,2H), 3.4–3.8 (m,4H), 4.45 (m,2+2H), 4.90 (d,1H), 5.55 (s,1H), 5.70 (d,1H), 6.75 (d,2H), 7.25(d,2H), 8.05 (s,1H), 3.0–3.65 (m,8H). |
| 14 | HO—⟨⟩— | —NH—⟨⟩—SO$_2$NH$_2$ | H | triazinone with CH$_3$ (N-methyl, OH, =O) | 44 | 1760 1665 1605 | 3.40(s,3H), 3.55 (m,2H), 4.25 (m,2H), 4.90 (d,1H), 5.55 (s,1H), 5.70 (d,1H), 6.85 (d,2H), 7.25 (d,2H), 7.70 (d,2H), 8.05 (d,2H), 8.36 (s,1H). |
| 15 | HO—⟨⟩— | —NH—⟨⟩—SO$_2$NH$_2$ | H | triazole with C$_2$H$_5$ | 52 | 1760 1670 1650 | 1.0(t,3H), 3.6 (m,2H), 4.4 (m,4H), 4.90 (d,1H), 5.50 (s,1H), 5.65 (d,1H), 6.75 (d,2H), 7.25 (d,2H), 7.70 (d,2H), 8.0 (d,2H), 8.35 (s,1H). |
| 16 | HO—⟨⟩— | —▷ (cyclopropyl) | H | triazole with CH$_2$CH$_2$CONH$_2$ | 59.5 | 1760 1660 1605 | 1.20(m,4H), 1.95 (m,1H), 3.0 (m,2H), 3.55 (m,2H), 4.35 (m,4H), 4.95 (d,1H), 5.55 (s,1H), 5.70 (d,1H), 6.75 (d,2H), 7.25 (d,2H), 8.40 (s,1H). |
| 17 | HO—⟨⟩— | —NH—⟨cyclohexyl⟩—OH | H | triazole with CH$_2$COCH$_3$ | 38 | 1760 1660 1610 | 1.75(m,8H), 2.20 (s,3H), 3.50–3.8 (m,4H), 4.0–4.4 (m,4H), 4.90 (d,1H), 5.55 (s,1H), 5.70 (d,1H), 6.75 (d,2H), 7.25 (d,2H), 8.05 (s,1H). |
| 18 | HO—⟨⟩— | —NHC$_3$H$_7$ | H | triazole with CH$_2$CH$_2$NHSO$_2$NH$_2$ | 53 | 1760 1670 1600 | 1.0(t,3H), 1.6 (q,2H), 3.0–3.6 (m,6H), 4.35 (m,4H), 4.95 (d,1H), 5.55 (s,2H), 5.70 (d,1H), 6.75 (d,2H), 7.25 (d,2H), 8.10 (s,1H). |

EXAMPLE 19

Sodium 7-{D-α-[(3-(2-p-aminosulfonylanilino-4-hydroxy-5-pyrimidinyl)-ureido]-p-hydroxyphenylacetamido}-3-[(1-(2'-aminoethyl)-tetrazol-5-yl)-thiomethyl]-ceph-3-em-4-carboxylate This compound was prepared in analogy to Example 1 from the ureidocarboxylic acid used in that example and an equimolar quantity of diphenylmethyl 7-amino-3-{[1-(2'-t-butoxycarbonylaminoethyl)-tetrazol-5-yl]-thiomethyl}-ceph-3-em-4-carboxylate. Yield after removal of the protective group and preparation of the sodium salt: 43.5%.

IR-spectrum: 1760, 1675, 1600 cm$^{-1}$; NMR-spectrum (DMSO+CD$_3$OD) signals at ppm: 3.15 (m, 2H), 3.55 (m, 2H), 4.35 (m, 4H), 4.95 (d, 1H), 5.55 (s, 1H), 5.70 (d, 1H), 6.75 (d, 2H), 7.25 (d, 2H), 7.70 (d, 2H), 8.0 (d, 2H), 8.35 (s, 1H).

EXAMPLE 20

Sodium 7-β-{D-α-[3-(2-p-aminosulfonylanilino-4-hydroxy-5-pyrimidinyl)-ureido]-p-hydroxyphenylacetamido}7α-methoxy-3-[(1-vinyl-tetrazol-5-yl)-thiomethyl]-ceph-3-em-4-carboxylate 960 mgm of the diphenylmethyl ester obtained in Example 1 were introduced into a mixture of 40 ml of anhydrous methanol and 10 ml of anhydrous tetrahydrofuran. A solution of lithium methoxide containing 7 mmols was added at −70° C. After stirring for 5 minutes, 0.18 ml of tert. butyl hypochlorite was added to the solution. The mixture was stirred for 30 minutes at −70° C., after which 0.45 ml of acetic acid and 0.15 ml of triethyl phosphite were added. The mixture was then allowed to return to room temperature after which the suspension was evaporated in vacuo to dryness. The solid product left behind was extracted twice with 50 ml of methanol and once with 450 ml of methylene chloride and suction-filtered off. For purification, it was chromatographed, using a prepared column (eluant: methylene chloride/methanol 6:1). Yield after removal of the protective group: 37%.

IR-spectrum: 1760, 1670, 1600 cm$^{-1}$; NMR-spectrum (DMSO+CD$_3$OD) signals at ppm: 3.45 (s, 3H), 3.55 (m, 2H), 4.35 (M, 2H), 5.0 (s, 1H), 5.40–5.90 (m, 3H), 6.6–7.0 (m, 2+1H), 7.15 (d, 2H), 7.7 (d, 2H), 8.0 (d, 2H), 8.35 (s, 1H).

EXAMPLE 21

Sodium 7β-{D,L-α-[3-(2-p-aminosulfonylanilino-4-hydroxy-5-pyrimidinyl)-ureido]-2-thienylacetamido}-7α-methoxy-3-[1-(vinyltetrazol-5-yl)-thiomethyl]-ceph-3-em-4-carboxylate The synthesis of this compound was carried out in the same way as in Example 20, starting from the cephalosporin diphenylmethyl ester which was obtained as an intermediate product in Example 4. Yield: 29%. IR-spectrum: 1760, 1660, 1600 cm$^{-1}$.

EXAMPLE 22

Sodium 7-{D-α-[3-(4-hydroxy-2-p-hydroxybenzylamino-5-pyrimidinyl)-ureido]-p-hydroxyphenylacetamido}-3-[(1-(2'-hydroxyethyl)-tetrazol-5-yl)-thiomethyl]-ceph-3-em-4-carboxylate 2.08 gm (62%) of 7-{D-α-[3-(4-hydroxy-2-p-hydroxybenzylamino-5-pyrimidinyl)-ureido]-p-hydroxyphenylacetamido}-3-acetoxymethyl-ceph-3-em-4-carboxylic acid were obtained as in Example 10 from 2.18 gm of D-α-[3-(4-hydroxy-2-p-hydroxybenzylamino-5-pyrimidinyl)-ureido]-p-hydroxyphenyl acetic acid (0.005 mol) and 1.36 gm of 7-aminocephalosporanic acid.

500 mgm of this cephalosporin were heated in an atmosphere of nitrogen for 6 hours at 70° C. with 200 mgm of 1-(2'-hydroxyethyl)-5-mercapto-tetrazole in 20 ml of a phosphoric acid buffer solution having a pH of 6.3, the pH-value being kept between 6 and 6.5. Thereafter, the reaction mixture was cooled, filtered off from some insoluble matter, and extracted twice with ethyl acetate. Hydrochloric acid was then added, while cooling, to a pH value of 2.8. The precipitated product was suction-filtered off, washed with a little water and dried. The residue was converted into the sodium salt in the usual way. Yield: 64%.

IR-spectrum: 1760, 1660, 1600 cm$^{-1}$; NMR-spectrum: 3.0 (m, 2H), 3.50 (2H), 4.1–4.5 (m, 6H), 4.95 (d, 1H), 5.50 (s, 1H), 5.65 (d, 1H, 6.75 (d, 2H), 7.25 (d, 2H), 7.70 (d, 2H), 8.0 (d, 2H), 8.36 (s, 1H).

EXAMPLE 23

Sodium 7-{D-α-[3-(4-hydroxy-2-(4'-hydroxycyclohexylamino)-5-pyrimidinyl)-ureido]-p-hydroxyphenylacetamido}-3-[(1-(2'-methylsulfonylethyl)-tetrazol-5-yl)-thiomethyl]-ceph-3-em-4-carboxylate This cephalosporin was synthesized in the same way as in Example 22 from 7-{D-α-[3-(4-hydroxy-2-(4'-hydroxycyclohexylamino)-5-pyrimidinyl)-ureido]-p-hydroxyphenylacetamido}-3-acetoxymethyl-ceph-3-em-4-carboxylate acid and 1-(2'-methylsulfonylethyl)-5-mercapto-tetrazole. Yield: 48.5% of theory.

IR-spectrum: 1760, 1600 cm$^{-1}$; NMR-spectrum (DMSO+CD$_3$OD) signals at ppm: 1.8 (m, 8H), 2.85 (s, 3H), 3.3–4.0 (m, 6H), 4.35 (m, 4H), 4.95 (d, 1H), 5.55 (s, 1H), 5.70 (d, 1H), 6.75 (d, 2H), 7.25 (d, 2H), 8.05 (s, 1H).

EXAMPLE 24

Sodium 7-{D-α-[3-(4-hydroxy-2-(4'-hydroxycyclohexylamino)-5-pyrimidinyl)-ureido]-p-hydroxyphenylacetamido}-3-[(1-methyl-5,6-dioxo-1,3,4-triazin-2-yl)-thiomethyl]-ceph-3-em-4-carboxylate This compound was synthesized as in Example 23 from the cephalosporin derivative used in that example and 4-methyl-2-mercapto-5,6-dioxo-1,3,4-triazine. Yield: 66.5% of theory.

IR-spectrum: 1760, 1670, 1600 cm$^{-1}$; NMR-spectrum (DMSO+CD$_3$OD) signals at ppm: 1.8 (m, 8H), 3.5 (m, 2H+s, 3H), 4.35 (m, 2H), 4.90 (d, 1H), 5.50 (s, 1H), 5.65 (d, 1H), 6.75 (d, 2H), 7.25 (d, 2H), 8.05 (s, 1H).

EXAMPLE 25

Sodium 7-{D-α-[3-(2-p-aminosulfonylanilino-4-hydroxy-5-pyrimidinyl)-ureido]-p-hydroxyphenylacetamido}-3-[(1-(2'-methylsulfonylethylamino)-tetrazol-5-yl)-thiomethyl]-ceph-3-em-4-carboxylate This compound was synthesized as in Example 1 from the ureidocarboxylic acid used in that example and the corresponding cephalosporin benzhydryl ester. Yield: 49.5%.

IR-spectrum: 1765, 1660, 1590 cm$^{-1}$; NMR-spectrum (DMSO+CD$_3$OD) signals at ppm: 2.9 (s, 3H), 3.6 (m, 4H), 4.4 (m, 4H), 5.0 (d, 1H), 5.4 (s, 1H), 5.75 (d, 1H), 6.8 (d, 2H), 7.3 (d, 2H), 7.8 (s, 1H), 8.32 (s, 1H).

The following compounds were analogously synthesized:

| Example | A | R | Y | Het | IR-spectrum (cm$^{-1}$) | NMR-spectrum (DMSO + CD$_3$OD) signals at ppm: |
|---|---|---|---|---|---|---|
| 26 | HO—⟨⟩— | —NH—⟨⟩—SO$_2$NH$_2$ | H | (tetrazole ring with N—CH$_2$CH$_2$NHCOCH$_3$) | 1760 1655 | 1.8 (s,3H), 3.5–3.7 (m,4H), 4.5 (m,2H), 4.9 (d,1H), 5.4 (s,1H), 5.60 (d,1H), 6.7 (d,2H), 7.2 (d,2H), 7.8 (q,4H), 8.35 (s,1H). |

-continued

| Example | A | R | Y | Het | IR-spectrum (cm⁻¹) | NMR-spectrum (DMSO + CD₃OD) signals at ppm: |
|---|---|---|---|---|---|---|
| 27 | HO—⟨ ⟩— | —NH—⟨ ⟩—SO₂NH₂ | H | N——N<br>‖<br>⟋N⟍N<br>        \|<br>   CH₂CH₂SOCH₃ | 1760<br>1660<br>1600<br>1150 | 2.6(s,3H), 3.2–3.6 (m,4H),<br>4.3 (m,2H), 4.65 (m,2H),<br>4.9 (d,1H), 5.4 (d,1H),<br>5.55 (d,1H), 6.65 (d,2H),<br>7.2 (d,2H), 7.65 (d,2H),<br>7.9 (d,2H), 8.30 (s,1H). |
| 28 | HO—⟨ ⟩— | —NH—⟨ ⟩—SO₂NH₂ | H | N——N<br>‖<br>⟋N⟍N<br>        \|<br>   CH₂CH₂SO₂CH₃ | 1760<br>1660<br>1600 | 3.0(s,3H), 3.45 (m,2H),<br>3.8 (m,2H), 4.2 (m,2H),<br>4.7 (m,2H), 4.85 (d,1H),<br>5.4 (s,1H), 5.6 (d,1H),<br>6.7 (d,2H), 7.3 (d,2H),<br>7.7 (d,2H), 8.0 (d,2H),<br>8.37 (s,1H). |

The compounds of the present invention, that is, those embraced by formulas I and I' and their non-toxic, pharmacologically acceptable salts, have useful pharmacodynamic properties. More particularly, they exhibit very effective antibacterial activity in warm-blooded animals, such as mice.

Cephalosporin antibiotics are widely used for the treatment of diseases which are caused by pathogenic bacteria in humans and in animals. Particularly, they can be used for the treatment of diseases caused by bacteria which are resistant against other antibiotics such as penicillin compounds, as well as for the treatment of penicillin-sensitive patients. In numerous cases it is desired to use a cephalosporin antibiotic which has a good activity against gram-positive and against gram-negative microorganisms. For that reason wide-ranging research has been performed with a view toward development of various types of cephalosporin antibiotics with a wide activity spectrum.

In these tests it has been found that it is difficult to find cephalosporin antibiotics which, besides a broad activity spectrum, also possess a good activity against strains of *pseudomonas aeruginosa*. Analogous to investigations in the field of penicillins, it has been tried to obtain pseudomonas-active cephalosporins by acylation of α-aminobenzyl cephalosporins, but it has been found that such compounds are usually not sufficiently active. Therefore, there is a further need to search for new cephalosporins which possess an increased activity against various strains of *pseudomonas aeruginosa* besides a broad activity spectrum.

As already mentioned, while intensive research work has been done with regard to acyl derivatives of α-aminobenzyl derivatives, only little has become known about derivatives where a heterocyclic aystem is bonded to the α-benzyl carbon atom of α-aminobenzyl cephalosporins via a ureido bridge (—NHCONH—). Only in German Offenlegungsschriften Nos. 2,710,979 and 2,650,826 cephalosporins are described, where pyridines or condensed pyridines are bonded to the cephalosporin nucleus in the way mentioned above.

These compounds, however, exhibit an insufficient activity against pseudomonas.

We have discovered that the compounds according to the present invention, with regard to their antibiotic activity, exhibit a broad activity spectrum together with an unusually good activity against pseudomonas strains. The high activity extends to numerous β-lactamase-forming gram-negative strains, as these compounds possess a high stability against β-lactamases which are formed from a series of gram-negative organisms.

Furthermore, the compounds according to the present invention are very well compatible. Therefore, they are useful for the prophylaxis and chemotherapy of local and systemic infections in both human and veterinary medicine.

Thus, for example, these compounds are useful for the treatment of diseases of the respiratory tract, the pharingeal cavity and urinary tract, particularly pharyngitis, pneumonia, peritonitis, pyelonephritis, otitis, cystitis, endocarditis, bronchitis, arthritis and general sytemic infections. Moreover, these compounds are useful as preservatives for inorganic or organic materials, especially for organic materials such as polymers, lubricants, dyes, fibers, leather, paper and wood, as well as foodstuffs.

As already indicated, this is made possible by the fact that the compounds of the present invention are highly active, both in vitro and in vivo, against harmful microorganisms, particularly against gram-positive and gram-negative bacteria and bacteria-like microorganisms, being distinguished in particular by a broad spectrum of activity.

Many local and/or systemic bacterial diseases can be treated and/or prevented by use of these cephalosporin derivatives of the present invention. Examples of such diseases include but are not limited to those caused by the following microorganisms:
Micrococcaceae, such as staphylococci;
Lactobacteriaceae, such as streptococci;
Corynebacteriaceae, such as corynebacteria;
Enterobacteriaceae, such as escherichiae bacteria of the coli group;
Klebsiella bacteria, such as *K. pneumoniae;*
Proteae bacteria of the proteus group, such as *proteus vulgaris;*
Salmonella bacteria, such as thyphimurium;
Shigella bacteria, such as *shigella dysenteriae;*
Pseudomonas bacteria, such as *pseudomonas aeruginosa;*
Aeromonas bacteria, such as *aeromonas lique faciens;*
Spirillaceae such as vibrio bacteria, such as *vibrio cholerae;*
Parvobacteriaceae or brucellaceae, such as pasteurella bacteria;
Brucella bacteria, such as *brucella abortus;*
Neisseriaceae, such as neisseria;
Haemophilus bacteria, such as *haemophilus influenzae;*
Bordetella bacteria, such as *bordetella pertussis;*
Moraxella bacteria, such as *moraxella lacunata;*

Bacteroidaceae, such as *bacteroides bacteria;*
Fusiforme bacteria, such as *fusobacterium fusiforme;*
Sphaerophorus bacteria, such as *sphaerophorus necrophorus;*
Bacillaceae, such as aerobic spore formers, like *bacillus antracis;*
Anerobe spore formers chlostridia, such as *chlostridium perfringens;*
Spirochaetaceae, such as *borrelia bacteria;*
Treponema bacteria, such as treponema pallidum; and
Leptospira bacteria, such as *leptospira interrogans.*

Specific examples of compounds of the present invention, which exhibit broad spectrum antibacterial activity against gram-positive and gram-negative bacteria as well as against pseudomonas are those of the formula

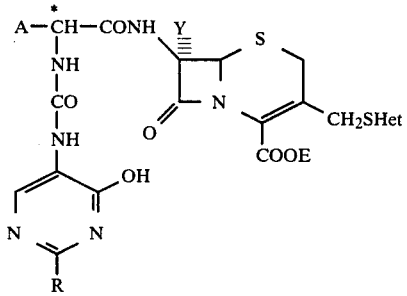

shown in the following table:

|     | A | R | Y | Het |
|-----|---|---|---|-----|
| (1) | HO—⟨⟩— | —NH—⟨⟩—SO₂NH₂ | H | $\underset{\underset{CH=CH_2}{|}}{N}$-triazole |
| (2) | HO—⟨⟩— | —NH—⟨⟩—SO₂NH₂ | H | triazole-$CH_2CH=CH_2$ |
| (3) | HO—⟨⟩— | —NH—⟨⟩—SO₂NH₂ | H | triazole-$CH_2CH_2NH_2$ |
| (4) | HO—⟨⟩— | —NH—⟨⟩—SO₂NH₂ | H | triazole-$CH_2CH_2N(CH_3)_2$ |
| (5) | HO—⟨⟩— | —NH—⟨⟩—SO₂NH₂ | H | triazole-$CH_2COOH$ |
| (6) | HO—⟨⟩— | —NH—⟨⟩—SO₂NH₂ | H | triazole-$CH_2CONH_2$ |
| (7) | HO—⟨⟩— | —NH—⟨⟩—SO₂NH₂ | H | triazole-$CH_2CH_2OH$ |
| (8) | HO—⟨⟩— | —NH—⟨⟩—SO₂NH₂ | H | triazole-$CH_2CH_2NHSO_2NH_2$ |

-continued

| | A | R | Y | Het |
|---|---|---|---|---|
| (9) | HO–⟨C6H4⟩– | –NH–⟨C6H4⟩–SO2NH2 | H | tetrazole with CH3 and N–CH2SO3H |
| (10) | ⟨thienyl⟩– | –NH–⟨C6H4⟩–SO2NH2 | H | tetrazole with CH3 and N–CH2CH2–OH |
| (11) | ⟨thienyl⟩– | –NH–⟨C6H4⟩–SO2NH2 | OCH3 | tetrazole with CH3 and N–CH2CH2OH |
| (12) | HO–⟨C6H4⟩– | –NH–⟨C6H4⟩–SO2NH2 | OCH3 | tetrazole with CH3 and N–CHCH2OH |
| (13) | HO–⟨C6H4⟩– | –NH–⟨C6H4⟩–SOCH3 | H | tetrazole with CH3 and N–CH2CH2OH |
| (14) | HO–⟨C6H4⟩– | –NH–⟨C6H4⟩–OH | H | tetrazole with CH3 and N–CH2NHSO3H |
| (15) | HO–⟨C6H4⟩– | –NH–⟨C6H4⟩–CONH2 | H | triazinone with CH3, OH, =O, N–CH3 |
| (16) | HO–⟨C6H4⟩– | –NH–⟨C6H4⟩–SO2NH2 | H | triazinone with CH3, OH, =O, N–CH3 |
| (17) | HO–⟨C6H4⟩– | –NH–⟨C6H4⟩–SO2NH2 | OCH3 | triazinone with CH3, OH, =O, N–CH3 |
| (18) | HO–⟨C6H4⟩– | –NHCH2–⟨C6H4⟩–OH | H | tetrazole with CH3 and N–CH2CH2OH |
| (19) | HO–⟨C6H4⟩– | –NHCH2–⟨C6H4⟩–OH | H | tetrazole with CH3 and N–CH2CH2NHCONH2 |

-continued

| | A | R | Y | Het |
|---|---|---|---|---|
| (20) | HO-C6H4- | -NHCH2-C6H4-SO2NH2 | H | 1-(CH2CH=CH2)-5-methyltetrazol-yl |
| (21) | HO-C6H4- | -NH-C6H4-SO2NH2 | H | 1-(CH2CH2SOCH3)-5-methyltetrazol-yl |
| (22) | HO-C6H4- | -NH-C6H10-OH | H | 1-(CH2CH2SO2CH3)-5-methyltetrazol-yl |
| (23) | HO-C6H4- | -NH(CH2)3OH | H | 1-(CH=CH2)-5-methyltetrazol-yl |
| (24) | HO-C6H4- | -NHCH2CH2SO2NH2 | H | 1-(CH2CH2NHCOCH3)-5-methyltetrazol-yl |
| (25) | HO-C6H4- | -NHC3H7 | H | 1-(CH2CH2NHSO2NH2)-5-methyltetrazol-yl |
| (26) | HO-C6H4- | -cyclopropyl | H | 1-(CH2CH2CONH2)-5-methyltetrazol-yl |
| (27) | HO-C6H4- | -NH-C6H10-OH | H | 1-(CH2COCH3)-5-methyltetrazol-yl |
| (28) | HO-C6H4- | -NH-C6H10-OH | H | 3-methyl-6-methyl-5-hydroxy-2-oxo-2,3-dihydro-1,2,4-triazine-yl (with COOH) |
| (29) | HO-C6H4- | -NH-C6H4-SO2NH2 | H | 1-(C2H5)-5-methyltetrazol-yl |

-continued

| | A | R | Y | Het |
|---|---|---|---|---|
| (30) | HO–⟨⟩– | –NH–⟨⟩–SO₂NH₂ | H | [triazole ring]<br>CH₂CH₂SO₂CH₃ |
| (31) | HO–⟨⟩– | –NH–⟨⟩–SO₂NH₂ | H | [triazole ring]<br>CH₂CH–CH₂OH<br>   \|<br>   OH |
| (32) | HO–⟨⟩– | –NH–⟨⟩(OH)–SO₂NH₂ | H | [triazole ring]<br>CH₂CH₂OH |
| (33) | HO–⟨⟩– | –NH–⟨⟩–SO₂NH₂ | H | CH₃–N–N–OH / N=O ring |
| (34) | ⟨⟩– | –NH–⟨⟩–SO₂NH₂ | OCH₃ | [triazole ring]<br>CH₂CH₂OH |
| (35) | HO–⟨⟩– | –NHCH₂–⟨⟩–SO₂NH₂ | H | [triazole ring]<br>CH₂CH₂OH |
| (36) | HO–⟨⟩– | –NH–⟨⟩–SO₂NH₂ | H | [triazole ring]<br>CH₂CH₂NHSO₂CH₃ |
| (37) | HO–⟨⟩– | –NH–⟨⟩–SO₂NH₂ | H | [triazole ring]<br>CH₂CH₂NHCOCH₃ |

The antibiotic activities of the compounds of the present invention were ascertained by the following test methods:

1. In vitro tests:

The tests were performed using the serial dilution test in the microtiter system. The effect of the test compound on bacteristasis was examined in a liquid medium at the following concentrations: >64, 64 32, 16, 8, 4, 2, 1, 0.5, 0.25, 0.125, 0.06, 0.03 and 0.015 μgm/ml. The nutrient medium consisted of 10 gm of peptone, 8 gm of meat extract oxoid, 3 gm of sodium chloride, and 2 gm of sec. sodium phosphate diluted with distilled water to 100 ml (pH 7.2–7.4). Only in the test against streptococci 1% of glucose was added. The age of the primary cultures was approximately 20 hours. The standardization of the bacteria suspension was effected using a photometer according to the method of Eppendorf (test tube φ-mm, filter 546 nm), using for comparison a barium sulfate suspension formed by the addition of 3.0 ml of 1% barium chloride solution to 97 ml of 1% sulfuric acid. After standardization, the test microorganisms were further diluted to a concentration of 1:1500, using a sodium chloride solution.

16 mgm of the particular test compound were put into a 10 ml measuring flask, and the flask was subsequently filled to the mark with solvent. The further dilution series was standardized with distilled water or the appropriate solvent.

The cavities of the microtiter plates were filled with 0.2 ml of nutrient medium. 0.01 ml of the appropriate test compound solution was then added, followed by inoculation with 0.01 ml (1 drop) of the standardized bacteria suspension. The bacteria were incubated at 37° C. for 18 to 20 hours. Control tests using only the solvent were carried out simultaneously.

The readings were made macroscopically to determine the minimum inhibitory concentration (the lowest still bacteriostatically effective concentration).

The following test organisms were used:

Staphylococcus aureus SG 511, Escherichia coli ATCC11 775, Pseudomonas aeruginosa hamburgensis and Pseudomonas aeruginosa BC 19, Serratia marcescens ATCC 13 880, Klebsiella pneumoniae ATCC 10 031 and BC 6, Proteus mirabilis BC 17, Proteus rettgeri BC 7, Enterobacter Cloaceae ATCC 13047 and E. coli R+TEM ($\beta$-lactamase carrier).

Table 2 below shows the minimum inhibiting concentrations (MIC) determined for typical representatives of the compounds according to the invention (the numbering corresponds to that used in Table 1).

Two typical commercially available cephalosporins were used as comparison compounds.

TABLE 3-continued

| In vivo activity in mice | |
|---|---|
| Cefuroxim | >100 |

(b) *Pseudomonas* (s.c. administration):

| Compound | ED$_{50}$ (mg$^+$/kg) |
|---|---|
| 7 | 6.3 |
| 16 | 10-20 |
| 30 | 10-20 |
| Cefuroxim | at 200 mg/kg, all the test animals died |

$^+$per dose

These values also show a significant superiority of compounds of the present invention over the comparison substance.

For pharmaceutical purposes the compounds of the present invention are administered to warm-blooded

TABLE

MIC-values of various cephalosporins (in µg/ml)

| Compound | S. aureus SG 511 | E. coli ATCC 11775 | Pseud. aerug. Hbg. | Pseud. aerug. BC 19 | Klebs. pneum. ATCC 10031 | Klebs. pneum. BC 6 | Prot. mir. BC 17 | Prot. rettg. BC 7 | Eb. cloaceae | E. coli R + TEM | Ser. marcesc. ATCC 13880 |
|---|---|---|---|---|---|---|---|---|---|---|---|
| Cefuroxim | 1 | 8 | >100 | >100 | 2 | 4 | 0.5 | 2 | 32 | 4 | 8 |
| Cephazolin | 0.06 | 4 | >100 | >100 | 1 | 2 | 4 | >100 | >100 | 4 | >100 |
| 5 | 4 | 0.5 | 8 | 8 | 0.5 | 0.5 | 0.12 | 0.25 | 2 | 32 | 0.5 |
| 7 | 1 | 0.03 | 4 | 4 | 0.12 | 0.12 | 0.06 | 0.25 | 0.25 | 4 | 0.12 |
| 16 | 0.12 | 0.12 | 8 | 4 | 0.12 | 0.25 | 0.12 | 0.25 | 0.25 | 4 | 0.25 |
| 21 | 1 | 0.12 | 8 | 8 | 0.25 | 0.25 | 0.12 | 0.5 | — | 8 | 0.25 |
| 30 | 2 | 0.12 | 8 | 4 | 0.5 | 0.5 | 0.06 | 1 | 0.5 | 8 | 0.5 |
| 36 | 2 | 0.03 | 4 | 2 | 0.12 | 0.12 | 0.06 | 0.25 | 0.12 | 8 | 0.25 |
| 37 | 2 | 0.12 | 8 | 4 | 0.12 | 0.12 | 0.06 | 0.25 | 0.12 | 8 | 0.12 |

As can be seen from Table 2, the compounds of this invention are distinctly superior to the comparison compounds in their effectiveness against typical gram-negative hospital germs, retaining their effectiveness agains gram-positive germs. Their effectiveness against pseudomonas strains deserves particular emphasis.

Several of the compounds of this invention were tested in vivo against experimental infections in mice. *E. coli* ATCC 11 775 and *Pseudomonas aeruginosa* BC 19 were used as the pathogenic bacteria. An interaperitoneal infection was induced with 0.2 ml of a bacterial suspension (containing 5% of mucin). This corresponds to approximately $1.4 \times 10^6$ *E. coli* germs or to $1.3 \times 10^6$ pseudomonas germs per mouse. Female mice of the NMRI strain were divided up into groups of 10 animals of which 2 groups remained untreated while the remaining groups were subcutaneously administered various doses of the particular cephalosporins according to the invention for the purpose of determining the ED$_{50}$ (dose at which 50% of the animals survive). In the case of the *E. coli* infection, the treatment was applied once (1 hour after infection) while the pseudomonas infection was treated 3 times (1, 3 and 5 hours after infection).

In both cases, the observation period was 7 days. The results of these tests, carried out with typical representatives of the cephalosporins according to the invention, are shown in Table 3 below.

TABLE 3

| In vivo activity in mice | |
|---|---|

(a) *E. coli* infection (s.c administration):

| Compound | ED$_{50}$ (mg/kg) |
|---|---|
| 7 | ~0.3 |
| 16 | ~0.8 |
| 30 | ~0.6 | animals perorally, parenterally, topically or rectally as active ingredients in customary pharmaceutical compositions, that is, compositions consisting essentially of an inert pharmaceutical carrier and an effective amount of the active ingredient, such as tablets, coated tablets, capsules, granulates, suppositories, solutions, suspensions, emulsions, ointments, gels, creams, powders and sprays. The active ingredient or a mixture of different active ingredients of the formula I may be administered to both humans and animals. The daily dose is from 5 to 500 mgm/kg, preferably from 10 to 200 mgm/kg, body weight at intervals of 24 hours, optionally administered in the form of several single doses. A single dose will preferably contain the active ingredient according to the invention in amounts of from 1 to 250, especially 10 to 60 mg/kg body weight. Depending on the type and body weight of the patient to be treated, on the type and severity of the disease, on the type of preparation and on the route of administration as well as on the period or interval over which the administration takes place, it may, however, be necessary to deviate from the above dosages. Thus, it may be sufficient in some cases to administer less than the above-mentioned amount of active ingredient, while in other cases the above-mentioned amount of active ingredient must be exceeded. The optimum dosage and route of administration of the active ingredients which are necessary in each case can easily be determined by one skilled in the art.

If the new compounds are used as additives for animal feed, they can be administered in the usual concentrations and preparations together with the feed or with feed preparations or with drinking water. By means of such administration the infection by gram-negative or gram-positive bacteria can be prevented, improved and/or cured, and also a promotion of the growth and an improvement in the utilization of the feed can be achieved.

The following examples illustrate a few pharmaceutical dosage unit compositions comprising a compound of the present invention as an active ingredient and represent the best modes contemplated of carrying out the invention. The parts art parts by weight unless otherwise specified.

EXAMPLE 29

Tablets

The tablet composition is compounded from the following ingredients:

| | |
|---|---|
| Sodium 7-{D-α-[3-(2-p-amino-sulfonylanilino-4-hydroxy-5-pyrimidinyl)-ureido]-p-hydroxy-phenylacetamido}-3-[(1-vinyl-tetrazol-5-yl)-thiomethyl]-ceph-3-em-4-carboxylate | 2.0 parts |
| Lactose | 5.0 parts |
| Potato starch | 1.8 parts |
| Magnesium stearate | 0.1 parts |
| Talcum | 0.1 parts |
| Total | 9.0 parts |

The ingredients are admixed in conventional manner and the composition is compressed into 900 mgm-tablets in a tablet making machine. Each tablet is an oral dosage unit composition containing 200 mgm of the active ingredient.

EXAMPLE 30

Coated tablets

The tablet composition is compounded from the following ingredients:

| | |
|---|---|
| Sodium 7-{D-α-[3-(2-p-amino-sulfonylanilino-4-hydroxy-5-pyrimidinyl)-ureido]-p-hydroxy-phenylacetamido}-3-[(1-vinyl-tetrazol-5-yl)-thiomethyl]-ceph-3-em-4-carboxylate | 2.0 parts |
| Lactose | 5.0 parts |
| Potato starch | 1.8 parts |
| Magnesium stearate | 0.1 parts |
| Talcum | 0.1 parts |
| Total | 9.0 parts |

Preparation:

The ingredients are admixed in conventional manner, and the composition is compressed into 900 mgm-tablets which are subsequently coated with a thin shell consisting essentially of a mixture of sugar, potato starch, talcum, and tragacanth. Each coated tablet is an oral dosage unit composition containing 200 mgm of the active ingredient.

EXAMPLE 31

Gelatin capsules 500 mgm portions of finely milled pivaloylmethyl 7-{D-α-[3-(2-p-amino-sulfonylanilino-4-hydroxy-5-pyrimidinyl)-ureido]-p-hydroxy-phenylacetamido}-3-[(1-methyl-tetrazol-5-yl)-thiomethyl]-ceph-3-em-4-carboxylate are filled into hard gelatin capsules of suitable size.

EXAMPLE 32

Injectable solution

Under aseptic conditions, 251 gm of sodium 7-{D-α-[3-(2-p-amino-sulfonylanilino-4-hydroxy-5-pyrimidinyl)-ureido]-p-hydroxy-phenylacetamido}-3-[(1-vinyl-tetrazol-5-yl)-thiomethyl]-ceph-3-em-4-carboxylate are dissolved in 200 ml of distilled water suitable for injection, the solution is filtered through a Millipore filter (pore size: 0.22 μm), 2.0 ml-portions of the filtrate are filled into 10 cc-ampules, the contents are lyophilized, and the ampules are closed with a rubber stopper and sealed with an aluminum cap. Each of these dry ampules contains 250 mgm of the active ingredient (ampule A).

Likewise under aseptic conditions, 2.0 ml-portions of a physiological salt solution are filled into 2 cc-ampules which are then sealed (ampule B).

Prior to injection, the contents of ampule B are added to the contents of ampule A, whereby a solution suitable for intravenous injection is obtained.

EXAMPLE 33

Infusion solution 20 ml of distilled water suitable for injection are added to the contents of two ampules A of the preceding example, and the resulting solution is dissolved in 250 ml of an aqueous 5% solution of glucose suitable for injection, whereby a continuous infusion solution is obtained.

Any one of the other compounds embraced by formula I or a non-toxic, pharmacologically acceptable salt thereof may be substituted for the particular active ingredient in Examples 29 through 33. Likewise, the amount of active ingredient in these illustrative examples may be varied to achieve the dosage unit range set forth above, and the amounts and nature of the inert pharmaceutical carrier ingredient may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the tautomeric formulas

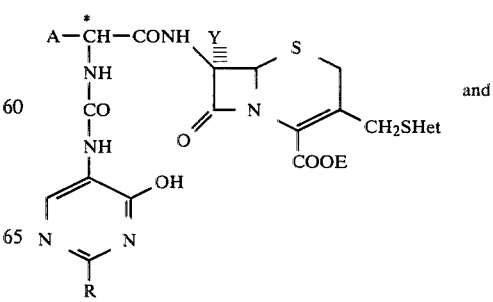

-continued

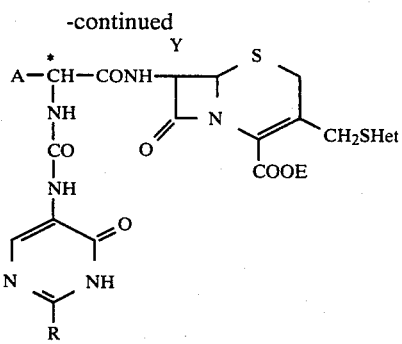

wherein
A is phenyl, 4-hydroxy-phenyl, 2-thienyl, 2-furyl or 3,4-dihydroxy-phenyl;
Y is hydrogen or methoxy;
Het is 4H-5,6-dioxo-1,2,4-triazin-3-yl, 4-methyl-5,6-dioxo-1,2,4-triazin-3-yl, 2-methyl-5,6-dioxo-1,2,4-triazin-3-yl, 1-vinyl-tetrazol-5-yl, 1-allyl-tetrazol-5-yl or

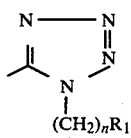

where
n is an integer from 1 to 3, inclusive,
$R_1$ is hydroxyl, amino, dimethylamino, acetylamino, aminocarbonyl, aminocarbonylamino, aminosulfonyl, aminosulfonylamino, methylcarbonyl, methylsulfonylamino, cyano, hydroxysulfonylamino, methylsulfonyl, methylsulfinyl, a carboxylic acid group or a sulfonic acid group, and
—$(CH_2)_n$—$R_1$ may also be alkyl of 2 to 4 carbon atoms or 2,3-dihydroxy-propyl;
R is cyclopropyl, 4'-hydroxycyclohexyl-amino,

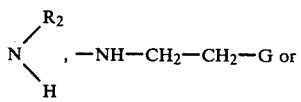 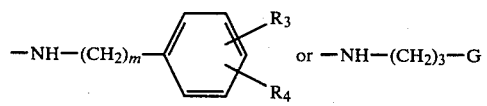

where
$R_2$ is straight or branched, saturated or unsaturated hydrocarbyl of 1 to 4 carbon atoms or cycloalkyl of 3 to 6 carbon atoms;
G is hydroxyl, aminocarbonyl, aminosulfonyl, aminocarbonylamino, acetylamino, methylsulfonylamino, methylsulfinyl or methylsulfonyl;
m is 0 or 1; and
$R_3$ and $R_4$ are each hydrogen, chlorine, fluorine, hydroxyl, methoxy, acetylamino, aminocarbonylamino, nitro, acetyl, methylcarbonyloxy, methoxycarbonyl, aminocarbonyl, cyano, methylsulfinyl, methylsulfonyl, aminosulfonyl, methylaminosulfonyl or methyl; and E is hydrogen or a protective group which is easily removable in vitro or in vivo;
or, when E is hydrogen, a non-toxic, pharmacologically acceptable salt thereof formed with an inorganic or organic base.

2. A compound of claim 1
where
A, R, Y and Het have the meanings defined in claim 1, and
E is hydrogen, or a non-toxic, pharmacologically acceptable salt thereof, formed with an inorganic or organic base.

3. A compound of claim 1,
where
A, Y, E and Het have the meanings defined in claim 1, and
R is p-aminosulfonyl-m-hydroxy-anilino, cyclopropyl, propylamino, isopropylamino, cyclopentylamino, cyclohexylamino, 3'-hydroxypropylamino, 4'-hydroxycyclohexyl-amino, 2'-aminosulfonylethyl-amino or

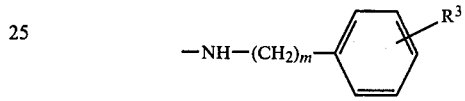

where
m is 0 or 1; and
$R_3$ is hydrogen, hydroxyl, nitro, acetylamino, methylsulfinyl, methylsulfonyl, acetyl, aminocarbonyl, aminocarbonylamino, aminosulfonyl or methylaminosulfonyl;
or, when E is hydrogen, a non-toxic, pharmacologically acceptable salt thereof formed with an inorganic or organic base.

4. A compound of claim 1,
where
A, R, Y and Het have the meanings defined in claim 1, and
E is benzyl, diphenylmethyl, trityl, tert. butyl, 2,2,2-trichloroethyl, trimethylsilyl, alkanoyloxyalkyl of 1 to 5 carbon atoms in the alkanoyl moiety and 1 to 3 carbon atoms in the alkylene moiety, phthalidyl or indanyl.

5. The compound of claim 1 which is sodium 7-{D-α-[3-(2-p-aminosulfonylanilino-4-hydroxy-5-pyrimidinyl)-ureido]-p-hydroxyphenylacetamido}-3-[(1-vinyl-tetrazol-5-yl)-thiomethyl]-ceph-3-em-4-carboxylate.

6. The compound of claim 1 which is sodium 7-{D-α-[3-(2-p-aminosulfonylanilino-4-hydroxy-5-pyrimidinyl)-ureido]-p-hydroxyphenylacetamido}-3-[(1-allyl-tetrazol-5-yl)-thiomethyl]-ceph-3-em-4-carboxylate.

7. The compound of claim 1 which is sodium 7-{D--α-[3-(2-p-aminosulfonylanilino-4-hydroxy-5-pyrimidinyl)-ureido]-p-hydroxyphenylacetamido}-3-[(4-methyl-5,6-dioxo-1,2,4-triazin-3-yl)-thiomethyl]-ceph-3-em-4-carboxylate.

8. The compound of claim 1 which is sodium 7-{D-α-[3-(2-p-aminosulfonylanilino-4-hydroxy-5-pyrimidinyl)-ureido]-p-hydroxyphenylacetamido}-3-{[1-(2'-dimethylaminoethyl)-tetrazol-5-yl]-thiomethyl}-ceph-3-em-4-carboxylic acid.

9. The compound of claim 1 which is the disodium salt of 7-{D-α-[3-(2-p-aminosulfonylanilino-4-hydroxy-5-pyrimidinyl)-ureido]-p-hydroxyphenylacetamido}-3-

[(1-carboxymethyl-tetrazol-5-yl)-thiomethyl]-ceph-3-em-4-carboxylic acid.

10. The compound of claim 1 which is sodium 7-{D-α-[3-(4-hydroxy-2-(4'-hydroxycyclohexylamino)-4-pyrimidinyl)-ureido]-p-hydroxyphenylacetamido}-3-[(1-vinyl-tetrazol-5-yl)-thiomethyl]-ceph-3-em-4-carboxylate.

11. The compound of claim 1 which is sodium 7-{D--α-[3-(2-p-aminosulfonylanilino-4-hydroxy-5-pyrimidinyl)-ureido]-p-hydroxyphenylacetamido}-3-{[1-(2'-hydroxyethyl)-tetrazol-5-yl]-thiomethyl}-ceph-3-em-4-carboxylate.

12. The compound of claim 1 which is sodium 7β--{D-α-[3-(2-p-aminosulfonylanilino-4-hydroxy-5-pyrimidinyl)-ureido]-p-hydroxyphenylacetamido}-7α-methoxy-3-[(1-vinyl-tetrazol-5-yl)-thiomethyl]-ceph-3-em-4-carboxylate.

13. An antibiotic pharmaceutical composition consisting essentially of an inert pharmaceutical carrier and an effective antibiotic amount of a compound of claim 1.

14. The method of inhibiting the growth of or destroying pathogenic bacteria in a warm-blooded animal in need thereof, which comprises perorally, parenterally, rectally or topically administering to said animal an effective antibiotic amount of a compound of claim 1.

* * * * *

UNITED STATES PATENT AND TRADEMARK OFFICE
CERTIFICATE OF CORRECTION

PATENT NO. : 4,362,725

DATED : December 7, 1982

INVENTOR(S) : BERND WETZEL ET AL.

It is certified that error appears in the above-identified patent and that said Letters Patent is hereby corrected as shown below:

Column 2, line 34: "pivaloylox-" should read -- pivaloyloxy- --.

Column 2, line 35: "ymethyl" should read -- methyl --.

Column 3: The portion of formula (I') which reads

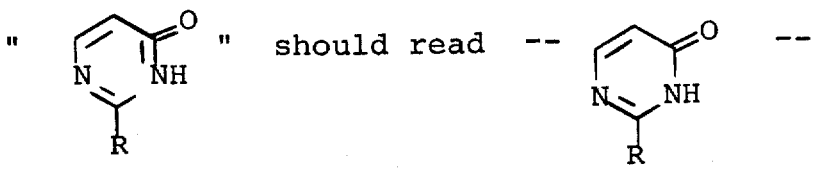

Column 7, line 36: "tha" should read -- than --.

Column 10, line 52; Column 17, line 41:
  "hydrox-" should read -- hydroxy- --.

Column 10, line 53: "ypyrimidines" should read -- pyrimidines --.

Column 12, line 24: "NMR-sectrum" should read -- NMR-spectrum --.

Column 13, line 15: "(002 mol)" should read -- (0.002 mol) --.

Column 13, line 16; Column 14, line 13; Column 18, line 45:
  "thi-" should read -- thio- --.

Column 13, line 17; Column 14, line 14; Column 18, line 46:
  "omethyl" should read -- methyl --.

UNITED STATES PATENT AND TRADEMARK OFFICE
CERTIFICATE OF CORRECTION

PATENT NO. : 4,362,725

DATED : December 7, 1982

INVENTOR(S) : BERND WETZEL ET AL.

It is certified that error appears in the above-identified patent and that said Letters Patent is hereby corrected as shown below:

Column 15, Example 16, correct the structural formula for "Het" to read -- 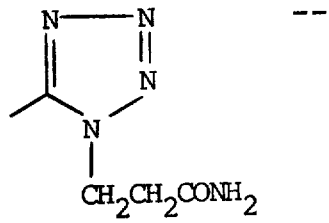 --

Column 17, line 18: "(M, 2H)" should read -- (m, 2H) --.

Column 17, line 42: "ybenzylamino" should read -- benzylamino --.

Column 18, line 5: After "d, 1H" insert ")" to read -- (d, 1H) --.

Column 18, line 18: "carboxylate acid" should read -- carboxylic acid --.

Column 24, Example 12, correct the structural formula for "Het" to read -- 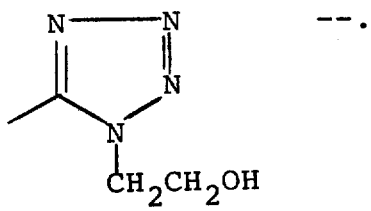 --.

UNITED STATES PATENT AND TRADEMARK OFFICE
CERTIFICATE OF CORRECTION

PATENT NO. : 4,362,725

DATED : December 7, 1982

INVENTOR(S) : BERND WETZEL ET AL.

It is certified that error appears in the above-identified patent and that said Letters Patent is hereby corrected as shown below:

Column 27, last line: "∅-mm" should read -- ∅ 14 mm --.

Column 33, first structural formula: The portion of that formula which reads

"  "  should read  --  --.

Signed and Sealed this

Fifteenth Day of March 1983

[SEAL]

Attest:

GERALD J. MOSSINGHOFF

Attesting Officer

Commissioner of Patents and Trademarks